US011690895B2

(12) United States Patent
Tyor et al.

(10) Patent No.: US 11,690,895 B2
(45) Date of Patent: Jul. 4, 2023

(54) COMPOSITIONS AND METHODS OF INTERFERON ALPHA BINDING PROTEINS

(71) Applicants: UNITED STATES GOVERNMENT AS REPRESENTED BY THE DEPARTMENT OF VETERANS AFFAIRS, Washington, DC (US); MEIOGEN BIOTECHNOLOGY CORPORATION, Somerville, MA (US)

(72) Inventors: William Tyor, Atlanta, GA (US); Rajeth Koneru, Cumming, GA (US); Jennifer Ward, Boston, MA (US); Leonard Maroun, Aurora, CO (US)

(73) Assignees: MEIOGEN BIOTECHNOLOGY CORPORATION, Somerville, MA (US); UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 16/755,699

(22) PCT Filed: Oct. 15, 2018

(86) PCT No.: PCT/US2018/055888
§ 371 (c)(1),
(2) Date: Apr. 13, 2020

(87) PCT Pub. No.: WO2019/075465
PCT Pub. Date: Apr. 18, 2019

(65) Prior Publication Data
US 2021/0196790 A1    Jul. 1, 2021

Related U.S. Application Data

(60) Provisional application No. 62/571,900, filed on Oct. 13, 2017.

(51) Int. Cl.
| A61K 31/4418 | (2006.01) |
| A61K 31/513 | (2006.01) |
| A61K 31/675 | (2006.01) |
| A61K 38/17 | (2006.01) |
| A61K 9/00 | (2006.01) |
| A61P 25/28 | (2006.01) |
| A61P 31/18 | (2006.01) |

(52) U.S. Cl.
CPC ........ *A61K 38/1793* (2013.01); *A61K 9/0019* (2013.01); *A61K 31/4418* (2013.01); *A61K 31/513* (2013.01); *A61K 31/675* (2013.01); *A61P 25/28* (2018.01); *A61P 31/18* (2018.01)

(58) Field of Classification Search
CPC combination set(s) only.
See application file for complete search history.

(56) References Cited

U.S. PATENT DOCUMENTS

| 5,780,027 A | 7/1998 | Maroun | |
| 7,285,526 B2 | 10/2007 | Maroun | |
| 7,887,814 B2 | 2/2011 | Maroun | |
| 2006/0194212 A1* | 8/2006 | Skurkovich | C07K 16/241 435/6.16 |
| 2007/0160609 A1* | 7/2007 | Maroun | C07K 16/249 424/145.1 |

OTHER PUBLICATIONS

Tyor et al., "the effects of a novel interferon inhibitor and a model of HIV encephalitis (P4. 308)," Neurology 82 (10 Suppl):P4. 308 (Apr. 2014) (Year: 2014).*
Fritz-French et al., "the recombinant vaccinia virus gene product, B18r, neutralizes interferon alpha and alleviates histopathological complications in an HIV encephalitis mouse model," Journal of interferon and cytokine research 34:510-518 (2014) (Year: 2014).*
Koneru et al., "Combined antiretroviral therapy reduces brain viral load and pathological features of HIV encephalitis in a mouse model," J. Neurovirol. 20:9-17 (2014) (Year: 2014).*
Yampolsky et al, The Exchangeability of Amino Acids in Proteins, Genetics, 2005, 170, pp. 1459-1472. (Year: 2005).*
Drumm et al, Genetic Variation and Clinical Heterogeneity in Cystic Fibrosis, Annu. Rev. Pathol. Mech. Dis., 2012, 7, pp. 267-282 (Year: 2012).*
Heaton RK, Clifford DB, Franklin DR, Jr., et al. HIV-associated neurocognitive disorders persist in the era of potent antiretroviral therapy: CHARTER Study. Neurology. Dec. 7, 2010;75(23):2087-96.
Antinori A, Arendt G, Becker JT, et al. Updated research nosology for HIV-associated neurocognitive disorders. Neurology. Oct. 3, 20070;69(18): 1789-99.
Saylor D, Dickens AM, Sacktor N, et al. HIV-associated neurocognitive disorderpathogenesis and prospects for treatment. Nat Rev Neurol. Apr. 2016;12(4):234-48.
Grant I, Franklin DR, Jr., Deutsch R, et al. Asymptomatic HIV-associated neurocognitive impairment increases risk for symptomatic decline. Neurology. Jun. 1, 20140;82(23):2055-62.

(Continued)

*Primary Examiner* — Julie Ha
*Assistant Examiner* — Kristina M Hellman
(74) *Attorney, Agent, or Firm* — Ballard Spahr LLP

(57) ABSTRACT

Disclosed are compositions comprising an interferon-alpha binding protein and combined anti-retroviral therapy (cART). In some aspects, the interferon-alpha binding protein is B18R. In some aspects, the compositions further comprise a pharmaceutically acceptable carrier. Disclosed are methods of treating a subject with HIV associated neurogenerative disorder (HAND) comprising administering a therapeutically effective amount of B18R and cART. Disclosed are methods of reversing behavioral abnormalities in subjects having HAND comprising administering a therapeutically effective amount of B18R.

5 Claims, 10 Drawing Sheets

Specification includes a Sequence Listing.

(56) References Cited

OTHER PUBLICATIONS

Rumbaugh JA, Tyor W. HIV-associated neurocognitive disorders: Five new things. Neurol Clin Pract. Jun. 2015;5(3):224-31.
Tyor WR, Power C, Gendelman HE, Markham Rb. A model of human immunodeficiency virus encephalitis in scid mice. Proc Natl Acad Sci USA. Sep. 1, 19935;90(18):8658-62.
Avgeropoulos N, Kelley B, Middaugh L, et al. SCID mice with HIV encephalitis develop behavioral abnormalities. J Acquir Immune Defic Syndr Hum Retrovirol. May 1, 1998;18(1):13-20.
Cook JE, Dasgupta S, Middaugh LD, et al. Highly active antiretroviral therapy and human immunodeficiency virus encephalitis. Ann Neurol, Jun. 2005;57(6):795-803,.
Cook-Easterwood J, Middaugh LD, Griffin WC, 3rd, Khan I, Tyor WR. Highly active antiretroviral therapy of cognitive dysfunction and neuronal abnormalities in SCID mice with HIV encephalitis. Exp Neurol. Jun. 2007;205(2):506-12.
Sas AR, Bimonte-Nelson HA, Tyor WR. Cognitive dysfunction in HIV encephalitic SCID mice correlates with levels of Interferon-alpha in the brain. AIDS. Oct. 1, 20078;21(16):2151-9.
Fritz-French C, Tyor W. Interferon-alpha (IFNalpha) neurotoxicity. Cytokine Growth Factor Rev. Feb. 2012-Apr. 23(l-2):7-14.
Anderson AM, Lennox JL, Mulligan MM, et al. Cerebrospinal fluid interferon alpha levels correlate with neurocognitive impairment in ambulatory HIV-Infected individuals. J Neurovirol. Feb. 2017;23(1):106-12.
Sas AR, Bimonte-Nelson H, Smothers CT, Woodward J, TyorWR. Interferon-alpha causes neuronal dysfunction in encephalitis. J Neurosci. 2009 Mar. 25;29(12):3948-55.
Fritz-French C, Shawahna R, Ward JE, Maroun LE, Tyor WR. The recombinant vaccinia virus gene product, B18R, neutralizes interferon alpha and alleviates histopathological complications in an HIV encephalitis mouse model. J Interferon Cytokine Res. Jul. 2014;34(7):510-7.
Kessing CF, TyorWR. Interferon-alpha induces neurotoxicity through activation of the type I receptor and the GluN2A subunit of the NMDA receptor. J Interferon Cytokine Res. Apr. 2015;35(4):317-24.
Tyor WR, Bimonte-Nelson H. A mouse model of HIV-associated neurocognitive disorders: a brain-behavior approach to discover disease mechanisms and novel treatments. J Neurovirol. Sep. 1, 20171.
Rui Y, Myers KR, Yu K, et al. Activity-dependent regulation of dendritic growth and maintenance by glycogen synthase kinase 3beta. Nat Commun. 2013;4:2628.
Zambon AC, Gaj S, Ho I, et al. GO-Elite: a flexible solution for pathway and ontology over-representation. Bioinformatics. Aug. 1, 20125;28(16):2209-10.
Rocca DL, Amici M, Antoniou A, et al. The small GTPase Arf1 modulates Arp2/3-mediated actin polymerization via PICK1 to regulate synaptic plasticity. Neuron. Jul. 2, 20134;79(2):293-307.
Koneru R, Olive MF, TyorWR. Combined antiretroviral therapy reduces brain viral load and pathological features of HIV encephalitis in a mouse model. J Neurovirol. Feb. 2014;20(1):9-17.
Symons JA, Alcami A, Smith GL. Vaccinia virus encodes a soluble type I interferon receptor of novel structure and broad species specificity. Cell. May 1, 19959;81(4):551-60.
Gringeri A, Musicco M, Hermans P, et al. Active anti-interferon-alpha immunization: a European-Israeli, randomized, double-blind, placebo-controlled clinical trial in 242 HIV-1-infected patients (the EURIS study). J Acquir Immune Defic Syndr Hum Retrovirol. Apr. 1, 1999;20(4):358-70.
Utay NS, Douek DC. Interferons and HIV Infection: The Good, the Bad, and the Ugly. Pathog Immun. 2016 Spring;1(1):107-16.
Benitez-King G, Ramirez-Rodriguez G, Ortiz L, Meza I. The neuronal cytoskeleton as a potential therapeutical target in neurodegenerative diseases and schizophrenia. Curr Drug Targets CNS Neurol Disord. Dec. 2004;3(6):515-33.
Lin YC, Koleske AJ. Mechanisms of synapse and dendrite maintenance and their disruption in psychiatric and neurodegenerative disorders. Annu Rev Neurosci. 2010;33:349-78.
Tadat, Sheng M. Molecular mechanisms of dendritic spine morphogenesis. Curr Opin Neurobiol. Feb. 2006;16(1):95-101.
Masliah E, Heaton RK, Marcotte TD, et al. Dendritic injury is a pathological substrate for human immunodeficiency virus-related cognitive disorders. HNRC Group. The HIV Neurobehavioral Research Center. Ann Neurol. Dec. 1997;42(6):963-72.
Taylor JM, Minter MR, Newman AG, Zhang M, Adlard PA, Crack PJ. Type-1 interferon signaling mediates neuro-inflammatory events in models of Alzheimer's disease. Neurobiol Aging. May 2014;35(5):1012-23.

* cited by examiner

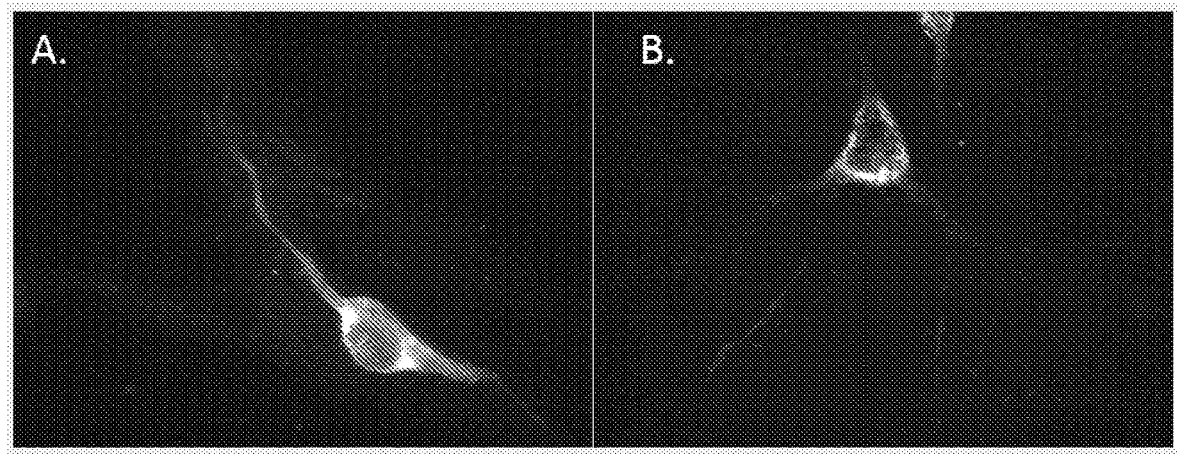
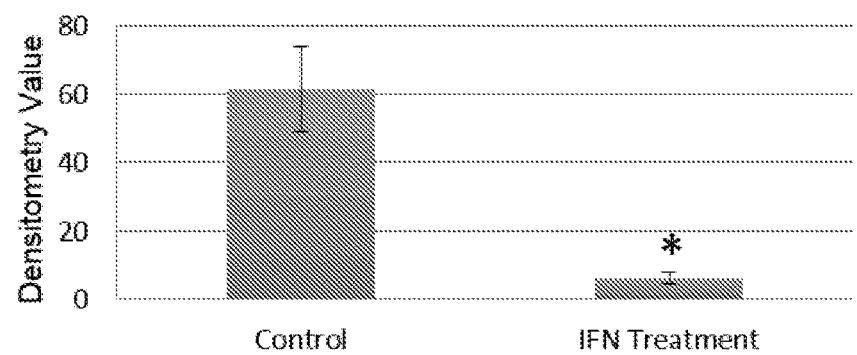
FIG. 7A, FIG. 7B, FIG. 7C

```
                        SEQUENCE LISTING

<160> NUMBER OF SEQ ID NOS: 1

<210> SEQ ID NO 1
<211> LENGTH: 351
<212> TYPE: PRT
<213> ORGANISM: Vaccinia virus

<400> SEQUENCE: 1

Met Thr Met Lys Met Met Val His Ile Tyr Phe Val Ser Leu Leu Leu
1               5                   10                  15

Leu Leu Phe His Ser Tyr Ala Ile Asp Ile Glu Asn Glu Ile Thr Glu
                20                  25                  30

Phe Phe Asn Lys Met Arg Asp Thr Leu Pro Ala Lys Asp Ser Lys Trp
            35                  40                  45

Leu Asn Pro Ala Cys Met Phe Gly Gly Thr Met Asn Asp Ile Ala Ala
        50                  55                  60

Leu Gly Glu Pro Phe Ser Ala Lys Cys Pro Pro Ile Glu Asp Ser Leu
65                  70                  75                  80

Leu Ser His Arg Tyr Lys Asp Tyr Val Val Lys Trp Glu Arg Leu Glu
                85                  90                  95

Lys Asn Arg Arg Arg Gln Val Ser Asn Lys Arg Val Lys His Gly Asp
            100                 105                 110

Leu Trp Ile Ala Asn Tyr Thr Ser Lys Phe Ser Asn Arg Arg Tyr Leu
        115                 120                 125

Cys Thr Val Thr Thr Lys Asn Gly Asp Cys Val Gln Gly Ile Val Arg
    130                 135                 140

Ser His Ile Arg Lys Pro Pro Ser Cys Ile Pro Lys Thr Tyr Glu Leu
145                 150                 155                 160

Gly Thr His Asp Lys Tyr Gly Ile Asp Leu Tyr Cys Gly Ile Leu Tyr
                165                 170                 175

Ala Lys His Tyr Asn Asn Ile Thr Trp Tyr Lys Asp Asn Lys Glu Ile
            180                 185                 190

Asn Ile Asp Asp Ile Lys Tyr Ser Gln Thr Gly Lys Glu Leu Ile Ile
        195                 200                 205

His Asn Pro Glu Leu Glu Asp Ser Gly Arg Tyr Asp Cys Tyr Val His
```

-continued

```
            210                 215                 220
Tyr Asp Asp Val Arg Ile Lys Asn Asp Ile Val Val Ser Arg Cys Lys
225                 230                 235                 240

Ile Leu Thr Val Ile Pro Ser Gln Asp His Arg Phe Lys Leu Ile Leu
                245                 250                 255

Asp Pro Lys Ile Asn Val Thr Ile Gly Glu Pro Ala Asn Ile Thr Cys
                260                 265                 270

Thr Ala Val Ser Thr Ser Leu Leu Ile Asp Asp Val Leu Ile Glu Trp
                275                 280                 285

Glu Asn Pro Ser Gly Trp Leu Ile Gly Phe Asp Phe Asp Val Tyr Ser
                290                 295                 300

Val Leu Thr Ser Arg Gly Gly Ile Thr Glu Ala Thr Leu Tyr Phe Glu
305                 310                 315                 320

Asn Val Thr Glu Glu Tyr Ile Gly Asn Thr Tyr Lys Cys Arg Gly His
                325                 330                 335

Asn Tyr Tyr Phe Glu Lys Thr Leu Thr Thr Thr Val Val Leu Glu
                340                 345                 350
```

COMPOSITIONS AND METHODS OF INTERFERON ALPHA BINDING PROTEINS

CROSS-REFERENCE TO RELATED APPLICATIONS

This is a U.S. National Phase Application of International Application No. PCT/US2018/055888, filed Oct. 15, 2018, which claims priority to and the benefit of the filing date of U.S. Provisional Patent Application No. 62/571,900, filed on Oct. 13, 2017, which are incorporated herein by reference in their entireties.

STATEMENT REGARDING FEDERALLY SPONSORED RESEARCH

This invention was made with government support under 1101BX001506-01 A2 awarded by the Department of Veterans Affairs. The government has certain rights in the invention.

BACKGROUND

HIV associated neurodegenerative disorders (HAND) occurs in up to 50% of roughly 35 million people living with HIV, even with combined antiretroviral therapy (cART). New therapeutic approaches are paramount. HAND includes asymptomatic neurocognitive impairment (ANI) and mild neurocognitive disorder (MND), which comprise most of the HAND disorders in cART treated patients. HIV associated dementia (HAD) is a more important condition in countries where cART is unavailable. According to the Antinori et al. criteria ANI and MND require neuropsychological testing. The underlying histopathology of ANI and MND are poorly understood compared to HAD. These factors are highly relevant to the development of HAND animal models because they dictate the need to incorporate behavioral measures. Novel treatments for HAND are currently needed.

BRIEF SUMMARY

Disclosed are compositions comprising an interferon-alpha (IFNα) binding protein and combined anti-retroviral therapy (cART). In some aspects, the IFNα binding protein is B18R or a variant thereof. In some aspects, the compositions further comprise a pharmaceutically acceptable carrier.

Disclosed are methods of treating a subject with HAND comprising administering a therapeutically effective amount of B18R or a variant thereof and cART.

Disclosed are methods of reversing behavioral abnormalities in subjects having HAND comprising administering a therapeutically effective amount of B18R or a variant thereof. Disclosed are methods of reversing behavioral abnormalities in subjects having HAND comprising administering a therapeutically effective amount of B18R or a variant thereof and cART.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 7A-7C show GLuR2 (AMPAR) immunofluorescent staining of control (A) and IFNα treated (B) DIV14 rat neurons. 100× photomicrographs. Densitometry was taken from 27 random images representative of 2 experiments (C). $*p=0.0000000000415$.

DETAILED DESCRIPTION

Figure 1A:
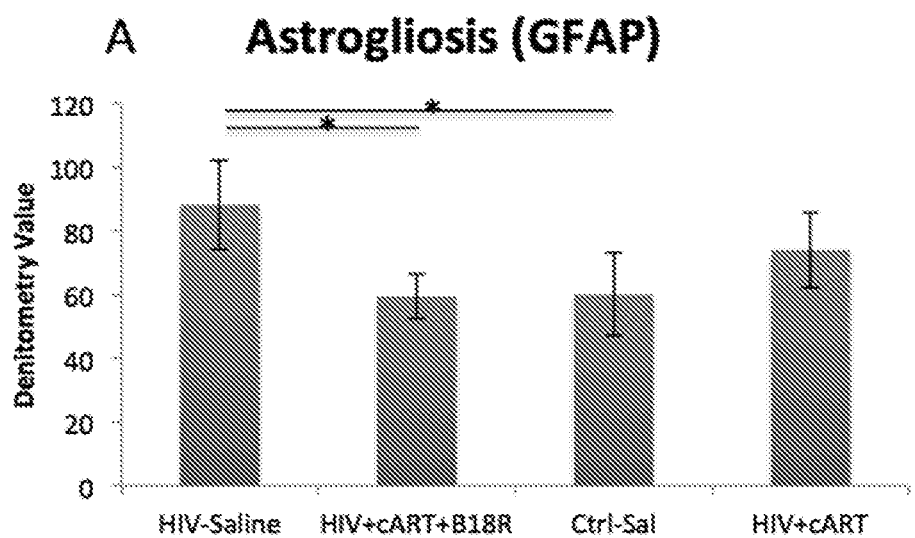
FIGS. 1A, 1B, and 1C show densitometry values for astrogliosis (A), microgliosis (B) and dendritic arborization (C). $*p<0.05$

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a subject" includes a plurality of such subjects, reference to "the IFNα binding protein" is a reference to one or more IFNα binding proteins and equivalents thereof known to those skilled in the art, and so forth.

As used herein, the term "therapeutically effective amount" means an amount of a therapeutic, prophylactic, and/or diagnostic agent that is sufficient, when administered to a subject suffering from or susceptible to a disease, disorder, and/or condition, to treat, alleviate, ameliorate, relieve, alleviate symptoms of, prevent, delay onset of, inhibit progression of, reduce severity of, and/or reduce incidence of the disease, disorder, and/or condition.

As used herein, the term "treating" refers to partially or completely alleviating, ameliorating, relieving, delaying onset of, inhibiting progression of, reducing severity of, and/or reducing incidence of one or more symptoms or features of a particular disease, disorder, and/or condition. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As used herein, the terms "inhibit," "inhibiting," and "inhibition" mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100 percent, or any amount of reduction in between as compared to native or control levels. In an aspect, the inhibition or reduction is 10-20, 20-30, 30-40, 40-50, 50-60, 60-70, 70-80, 80-90, or 90-100 percent as compared to native or control levels. In an aspect, the inhibition or reduction is 0-25, 25-50, 50-75, or 75-100 percent as compared to native or control levels. Further, the terms, "inhibit" or "inhibiting" mean decreasing tumor cell growth rate from the rate that would occur without treatment and/or causing tumor mass (e.g., cancer) to decrease. Inhibiting also include causing a complete regression of the tumor (e.g., cancer).

By "pharmaceutically acceptable carrier" is meant a diluent, excipient, or adjuvant which is physiologically acceptable to the subject while retaining the therapeutic properties of the composition with which it is administered. One exemplary pharmaceutically acceptable carrier is physiological saline. Other physiologically acceptable diluents, excipients, carriers, or adjuvants and their formulations are known to one skilled in the art.

The term "subject" or "patient" refers to any organism to which a composition of this invention may be administered, e.g., for experimental, diagnostic, and/or therapeutic purposes. Typical subjects include animals (e.g., mammals such as non-human primates, and humans; avians; domestic household or farm animals such as cats, dogs, sheep, goats, cattle, horses and pigs; laboratory animals such as mice, rats and guinea pigs) and/or plants. Typically, "subjects" are animals, including mammals such as humans and primates; and the like.

Subjects having HIV associated neurodegenerative disorder (HAND) refers to people living with HIV have learning and memory problems, which includes three disorders—asymptomatic neurocognitive impairment, mild neurocognitive disorder and HIV associated dementia (HAD).

As used herein, HAD, the most severe form of HAND, is where the patient's brain dysfunction makes them unable to accomplish everyday functions. HAD patients become increasingly unable to perform even rudimentary types of functions such as talking or walking and eventually death ensues.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Compositions

Disclosed are compositions comprising an IFNα binding protein and/or combined anti-retroviral therapy (cART). In some aspects, the IFNα binding protein can be virus-derived. In some aspects, the IFNα binding protein can be B18R or a variant thereof. In any of the compositions or methods disclosed throughout, the IFNα binding protein can be B18R or a variant thereof.

By "B18R" is meant the IFNα inhibitor protein termed B18R. In some aspects, B18R can be the sequence of Genbank #01019.1; SEQ ID NO:1. The B18R protein is a type I interferon receptor encoded by the B18R gene of the Western Reserve vaccinia virus strain. The 60-65 kD glycoprotein is related to the interleukin-1 receptors and is a member of the immunoglobulin superfamily, unlike other type I IFN-receptors, which belong to the class II cytokine receptor family. The B 18R protein has a high affinity (KD, 174 pM) for human IFNα and, unlike other type I IFN receptors, has broad species specificity, binding to type I interferons of human, mouse, rat, rabbit, pig, and cow. Among viral host response modifiers, the B18R protein is unique in that it exists as a soluble extracellular, as well as a cell surface protein, enabling blockage of both autocrine and paracrine IFN functions. The B18R protein has been shown to inhibit the antiviral potency of IFNα 1, IFNα 2, IFNα -8/1/8, and IFN-omega on human cells. In an aspect, the B18R protein has the sequence set forth in SEQ ID NO:1. In some aspects, B18R can be a homolog of the vaccinia virus produced B18R, such as B18R produced by the Orthopox and related families of viruses. The disclosed B18R proteins and variants thereof have the shared ability to strongly bind to, and inhibit, the IFNα family of cytokines. In an aspect, the B18R variant can have a greater than 70%, 80%, 90%, 95%, 96%, 97%, 98%, or 99% identity or similarity to SEQ ID NO: 1. In an aspect, the B18R variant can be a deletion mutant such as the deletion variant described in U.S. Pat. No. 9,861,681 which is hereby incorporated by reference in its entirety for its teaching of a B18R variant.

```
SEQ ID NO: 1 consists of the amino acid sequence
                                    ( SEQ ID NO: 1)
MTMKMMVHIYFVSLLLLLFHSYAIDIENEITEFFNKMRDTLPAKD

SKWLNPACMFGGTMNDIAALGEPFSAKCPPIEDSLLSHRYKDYVV

KWERLEKNRRRQVSNKRVKHGDLWIANYTSKFSNRRYLCTVTTKN

GDCVQGIVRSHIRKPPSCIPKTYELGTHDKYGIDLYCGILYAKHY

NNITWYKDNKEINIDDIKYSQTGKELIIHNPELEDSGRYDCYVHY

DDVRIKNDIVVSRCKILTVIPSQDHRFKLILDPKINVTIGEPANI

TCTAVSTSLLIDDVLIEWENPSGWLIGFDFDVYSVLTSRGGITEA

TLYFENVTEEYIGNTYKCRGHNYYFEKTLTTTVVLE.
```

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, J. Mol. Biol. 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna. CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4.

The term "variant" refers to polynucleotides or polypeptides described herein that are modified at one or more base pairs, codons, introns, exons, or amino acid residues (respectively) yet still retain the ability to bind to, and inhibit, the IFNα family of cytokines. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination thereof.

The term "saturation mutagenesis" or "GSSM" includes a method that uses degenerate oligonucleotide primers to introduce point mutations into a polynucleotide, as described in detail, below.

The term "optimized directed evolution system" or "optimized directed evolution" includes a method for reassembling fragments of related nucleic acid sequences, e.g., related genes, and explained in detail, below.

The term "synthetic ligation reassembly" or "SLR" includes a method of ligating oligonucleotide fragments in a non-stochastic fashion, and explained in detail, below.

"Combined anti-retroviral therapy" or "cART" refers to combination antiretroviral therapy. "Combined anti-retroviral therapy" or "cART" refers to the combinations of drugs that are used to keep HIV infections under control. These are also commonly referred to as highly active antiretroviral therapy (HAART) regimens and the terminology has further evolved to simply ART for antiretroviral therapy. The combination of anti-retrovirals used in cART can be changed based on drug sensitivities of the subject and drug resistance development.

Drug combinations used in cART can consist of a minimum of two active drugs from two classes. In some aspects they contain three or more different drugs.

Medications included in cART include, but are not limited to Nucleotide reverse transcriptase inhibitors (NRTIs), Non-nucleotide reverse transcriptase inhibitors (NNRTIs), Protease inhibitors (PIs), and Integrase inhibitors. Each type of drug can interfere with different stages of the HIV infection and replication process. For example, in some instances, cART comprises Atazanavir, Tenofovir, and Emtricitabine.

In some aspects, B18R and cART can be formulated together into a single composition. In some aspects, B18R and cART can be formulated independent of each other.

Disclosed are compositions comprising an IFNα binding protein and/or cART, further comprising a pharmaceutically acceptable carrier. In some aspects, the IFNα binding protein can be B 18R or a variant thereof.

As provided herein, B18R can be a protein produced by a gene from vaccinia virus that can inhibit the action of IFNα by strong binding. In some aspects, B18R can be produced by recombinant DNA procedures in bacterial cells. Any B18R variants that retain the function of binding IFNα can also be used in the disclosed compositions and methods. U.S. Pat. Nos. 5,780,027, 7,285,526 and 7,887,814 all provide examples of B18R and methods of making the same, all of which are hereby incorporated by reference in their entirety for their teaching of examples of B 18R and methods of making the same.

As disclosed herein, are pharmaceutical compositions, comprising B18R or a variant thereof and/or cART and a pharmaceutical acceptable carrier described herein. In some aspects, the B18R and/or cART can be formulated for oral or parental administration. In an aspect, the parental administration is intravenous, subcutaneous, intramuscular or direct injection. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The compositions can be administered directly to a subject. Generally, the compositions can be suspended in a pharmaceutically acceptable carrier (e.g., physiological saline or a buffered saline solution) to facilitate their delivery. Encapsulation of the compositions in a suitable delivery vehicle (e.g., polymeric microparticles or implantable devices) may increase the efficiency of delivery.

The compositions can be formulated in various ways for parenteral or nonparenteral administration. Where suitable, oral formulations can take the form of tablets, pills, capsules, or powders, which may be enterically coated or otherwise protected. Sustained release formulations, suspensions, elixirs, aerosols, and the like can also be used.

Pharmaceutically acceptable carriers and excipients can be incorporated (e.g., water, saline, aqueous dextrose, and glycols, oils (including those of petroleum, animal, vegetable or synthetic origin), starch, cellulose, talc, glucose, lactose, sucrose, gelatin, malt, rice, flour, chalk, silica gel, magnesium stearate, sodium stearate, glycerol monosterate, sodium chloride, dried skim milk, glycerol, propylene glycol, ethanol, and the like). The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in "Remington's Pharmaceutical Sciences" by E. W. Martin, which is herein incorporated by reference. Such compositions will, in any event, contain an effective amount of the compositions together with a suitable amount of carrier so as to prepare the proper dosage form for proper administration to the patient.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used. Thus, compositions can be prepared for parenteral administration that includes B18R and/or cART dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like).

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules.

C. Methods

1. Methods of Treating a Subject with HAND

Disclosed are methods of treating a subject with HAND comprising administering a therapeutically effective amount of an IFNα inhibitor comprised of a virus-derived IFNα binding protein. In some aspects, virus-derived IFNα binding protein can be B18R or a variant thereof.

Disclosed are methods of treating a subject with HAND comprising administering a therapeutically effective amount of B18R or a variant thereof and cART. In some aspects, methods of treating a subject with HAND can comprise administering a therapeutically effective amount of B18R or a variant thereof without cART.

Disclosed are methods of treating a subject with HAND comprising: identifying a patient in need of treatment; and administering a therapeutically effective amount of B 18R or a variant thereof and cART.

In some instances, identifying a subject in need of treatment comprises determining an increase of IFNα in the cerebrospinal fluid of the subject.

In some instances, a subject with HAND has previously undergone cART treatment without administering B 18R.

In some instances, the clinical effects of administering a therapeutically effective amount of B18R or a variant thereof and cART can be monitored by determining the levels of IFNα in the serum of the subject being treated.

2. Methods of Reversing Behavioral Abnormalities

Disclosed are methods of reversing behavioral abnormalities in subjects having HAND comprising administering a therapeutically effective amount of B18R or a variant thereof.

Disclosed are methods of reversing behavioral abnormalities in subjects having HAND comprising identifying a subject in need of treatment; and administering a therapeutically effective amount of B18R or a variant thereof and cART.

In some instances, identifying a subject in need of treatment comprises determining an increase of IFNα in the cerebrospinal fluid of the subject. In some instances, identifying a subject in need of treatment comprises clinical history and neuropsychological testing of the subject. In some instances, a identifying a subject in need of treatment comprises a combination of clinical history and neuropsychological testing of the subject and determining an increase of IFNα in the cerebrospinal fluid of the subject.

In some instances, a subject with HAND has previously undergone cART treatment without administering B 18R.

In some instances, the clinical effects of administering a therapeutically effective amount of B18R or a variant thereof can be monitored by determining the levels of IFNα in the serum of the subject being treated.

3. Methods of Reversing the Pathology of HIV Brain Infection

Disclosed are methods of reversing the pathology of HIV brain infection comprising administering a therapeutically effective amount of B18R or a variant thereof and cART.

Disclosed are methods of reversing the pathology of HIV brain infection comprising identifying a subject in need of treatment; and administering a therapeutically effective amount of B18R or a variant thereof and cART.

In some instances, identifying a subject in need of treatment comprises determining an increase of IFNα in the cerebrospinal fluid of the subject.

In some instances, the subject has previously undergone cART treatment without administering B18R.

In some instances, the clinical effects of administering a therapeutically effective amount of B18R or a variant thereof and cART can be monitored by determining the levels of IFNα in the serum of the subject being treated.

4. Methods of Improving the Learning and Memory Function in a Subject Infected with HIV Disclosed are methods of improving the learning and memory function in a subject infected with HIV comprising administering a therapeutically effective amount of B18R or a variant thereof and cART.

Disclosed are methods of improving the learning and memory function in a subject infected with HIV comprising identifying a patient in need of treatment; and administering a therapeutically effective amount of B18R or a variant thereof and cART.

In some instances, identifying a subject in need of treatment comprises determining an increase of IFNα in the cerebrospinal fluid of the subject. In some instances, identifying a subject in need of treatment comprises clinical history and neuropsychological testing of the subject. In some instances, a identifying a subject in need of treatment comprises a combination of clinical history and neuropsychological testing of the subject and determining an increase of IFNα in the cerebrospinal fluid of the subject.

In some instances, the subject infected with HIV has previously undergone cART treatment without administering B 18R.

In some instances, the clinical effects of administering a therapeutically effective amount of B18R or a variant thereof and cART can be monitored by determining the levels of IFNα in the serum of the subject being treated.

5. Administering

The disclosed methods comprise a step of administering a therapeutically effective amount of B18R or a variant thereof and cART. In some instances, administering a therapeutically effective amount of B18R or a variant thereof and cART occurs simultaneously. The B18R or a variant thereof and cART can be formulated independently but administered simultaneously. In some instances, B 18R or a variant thereof can be formulated with one or more of the antiretroviral compounds present in the cART. Simultaneous administration can be administration of the B18R or a variant thereof and cART at the exact same time, within about 5, 10, 15, 20, 25, 30, 35, 40, 45, 50, 55, or 60 minutes of each other. In some instances, B18R or a variant thereof and cART are administered within about 1, 2, 3, 4, 5, 6, 7, 8, 9, 10, 11, 12, 13, 14, 15, 16, 17, 18, 19, 20, 21, 22, 23 or 24 hours of each other. In some instances, B18R a or a variant thereof nd cART are administered within about 1, 2, 3, 4, 5, 6, or 7 days of each other. In some instances, B18R and cART are administered within about 1, 2, 3, or 4 weeks of each other. In some instances, B18R or a variant thereof and cART are administered within about 1, 2, 3, 4, 5, 6, 7, 8, 9, 10, 11, or 12 months of each other.

In some instances, both the B18R or a variant thereof and cART are administered subcutaneously. Other routes of administration include, but are not limited to, oral, intraperitoneal, buccal, nasal, or intravenous.

The compositions described herein can be formulated to include a therapeutically effective amount of B 18R or a variant thereof and cART described herein. In an aspect, the compositions described herein can be formulated to include a therapeutically effective amount of B18R or a variant thereof and cART described herein. Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to HAND, behavioral abnormalities associated with HAND, or pathology of HIV brain infection.

The compositions described herein can be administered to the subject (e.g., a human patient) in an amount sufficient to delay, reduce, or preferably prevent the onset of clinical disease. Accordingly, in some aspects, the patient can be a human patient. In therapeutic applications, compositions can be administered to a subject (e.g., a human patient) already with or diagnosed with cancer (or autoimmune disorder) in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a composition (e.g., a pharmaceutical composition) can be an amount that achieves a cure, but that outcome is only one among several that can be achieved. As noted, a therapeutically effective amount includes amounts that provide a treatment in which the onset or progression of/to HAND, behavioral abnormalities associated with HAND, or pathology of HIV brain infection is delayed, hindered, or prevented. One or more of the symptoms can be less severe. Recovery can be accelerated in an individual who has been treated.

The therapeutically effective amount or dosage of B18R or a variant thereof and cART or any component of B18R or a variant thereof and cART used in any of the methods as disclosed herein applied to mammals (e.g., humans) can be determined by one of ordinary skill in the art with consideration of individual differences in age, weight, sex, other drugs administered and the judgment of the attending clinician. Variations in the needed dosage may be expected. Variations in dosage levels can be adjusted using standard empirical routes for optimization. The particular dosage of a pharmaceutical composition to be administered to the patient will depend on a variety of considerations (e.g., the severity of the cancer or autoimmune disorder symptoms), the age and physical characteristics of the subject and other considerations known to those of ordinary skill in the art. Dosages can be established using clinical approaches known to one of ordinary skill in the art. In an aspect, the pharmaceutical formulation can be a unit dosage formulation.

The duration of treatment with any composition provided herein can be any length of time from as short as one day to as long as the life span of the host (e.g., many years). For example, the compositions can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present compositions can be administered once (or twice, three times, etc.) daily, weekly, monthly, or yearly.

The total effective amount of the compositions as disclosed herein can be administered to a subject as a single dose, either as a bolus or by infusion over a relatively short period of time, or can be administered using a fractionated treatment protocol in which multiple doses are administered over a more prolonged period of time. Alternatively, continuous intravenous infusions sufficient to maintain therapeutically effective concentrations in the blood are also within the scope of the present disclosure.

D. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits comprising B18R or a variant thereof and cART.

EXAMPLES

Example 1

HIV commonly causes HAND despite life-prolonging cART. Substantial evidence shows that IFNα plays a role in HAND pathogenesis. B18R, which binds IFNα, ameliorates HIV induced histopathology, including astrogliosis, microgliosis and reduced neuronal marker, in a HAND mouse model. In this report B18R with cART were co-administered and provide enhanced protection from the above encephalitis markers compared to cART alone in the HAND mouse model. In a separate set of experiments, B18R was tested for its ability to reverse behavioral abnormalities of HAND mice using an Object Recognition Test (ORT). The ORT was administered to HAND mice and controls before and after treatment with B 18R. HAND mice treated with B 18R showed significant improvement of behavioral impairment compared to untreated HAND mice. Because of its ability to act in concert with cART as well as reverse behavioral abnormalities in HAND mice, B18R is a therapeutic agent for HAND patients.

A decoy protein that sequesters type I interferons, B18R, ameliorates HIV induced histopathology in a HAND mouse model. An experiment was performed that examined whether B18R plus cART in HAND mice is better than cART alone in ameliorating histopathological markers in the brain. A second study examined whether B18R can reverse behavioral abnormalities in the HAND model.

A. Experiment 1

1. Materials and Methods

Primary human monocytes were split into 2 groups: HIV infected and uninfected (control groups). After 1 week in DMEM with M-CSF monocytes/macrophages were infected with 1ml HIV-ADA (MOI of 0.1) for 4 hours. Cells were collected 12 days after HIV infection and resuspended in sterile PBS for intracerebral (IC) inoculation into mice. Ninety percent of macrophages immunostained positive for p24 antigen prior to IC inoculation.

Four-week old B6.CB17-Prkdc$^{scid}$/SzJ male mice were injected IC in to the right frontal lobe with $10^5$ HIV-infected or uninfected macrophages. There were four groups of mice: control group receiving saline subcutaneously (SC) TID (n=6), HAND mice receiving saline SC TID (n=6), HAND mice receiving combined antiretroviral therapy (cART) SC TID (n=6), and HAND mice treated with cART SC TID and B18R SC BID (n=6). HAND mice in the cART group were given SC injections of 300 ul 75 mg/kg atazanvair TID. They were simultaneously given 120 ul of 75 mg/kg tenofovir/emtricitabine cocktail SC TID. HAND mice in the cART/B18R group were given cART described earlier plus 200 ul of 50 ug B18R BID. All mice received repeated SC injections for 10 days.

Mice were immediately sacrificed after the final injection and brains were extracted and snap frozen. Brains were cryosectioned (5 uM) coronally starting at the rostral end of the frontal cortex and ending ¾ through the cerebral hemispheres in the parieto-occipital area. Groups of sections were immunostained for human macrophages (EBM11), HIV (p24 antigen), astrocytes (GFAP), mononuclear phagocytes (CD45) and neurons (MAP2). Staining was assessed through microscopy and densitometry measurements. Viewers were blinded to treatment.

2. Results

Figure 1B:
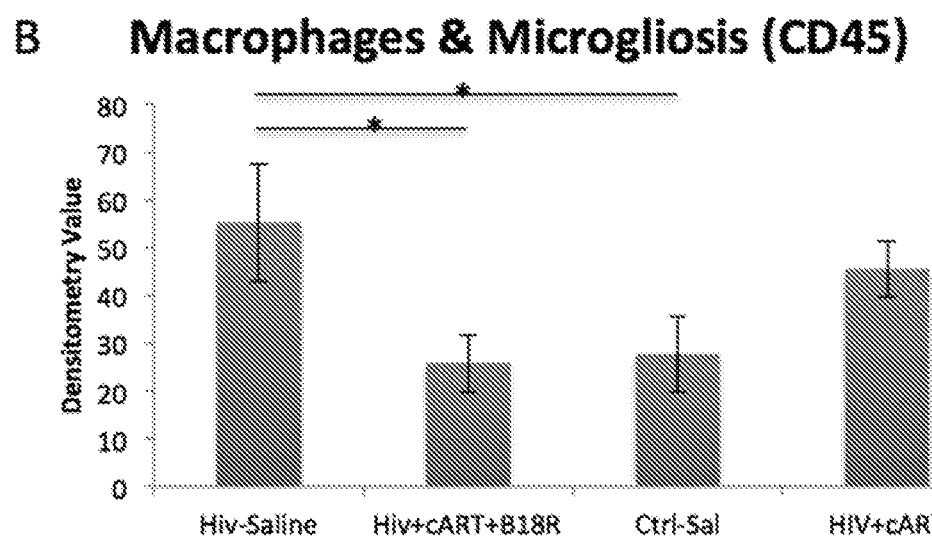
Figure 1C:
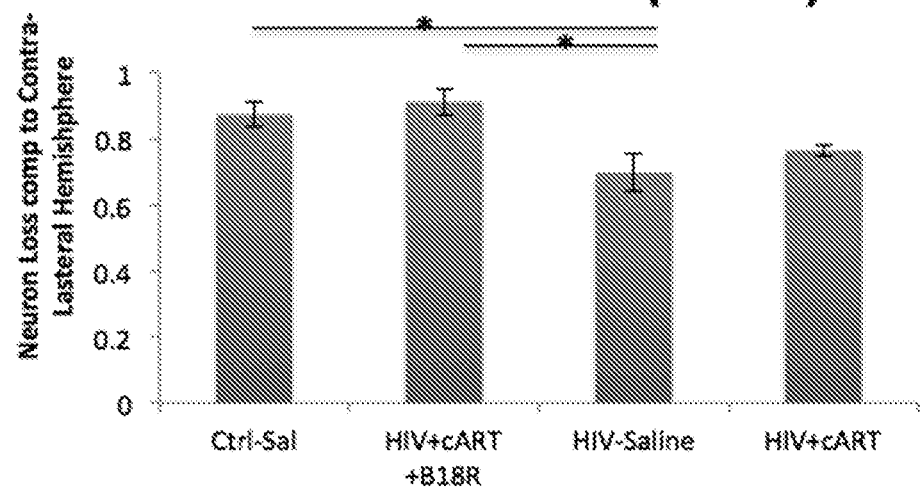

Astrogliosis was significantly decreased in B18R+cART treated HAND mice compared to untreated HAND mice (FIG. 1A). HAND mice treated with B18R and cART had significantly less immunostaining for mononuclear phagocytes (i.e. macrophages and microglia) than untreated HAND mice (FIG. 1B). Both astrogliosis and microgliosis were reduced to levels seen in control mice in HAND mice with B18R+cART treatment (FIGS. 1A and 1B). More importantly, B 18R+cART treated HIV mice were significantly protected against a reduction in dendritic arborization (FIG. 1C).

B. Experiment 2

1. Materials and Methods

Figure 2:
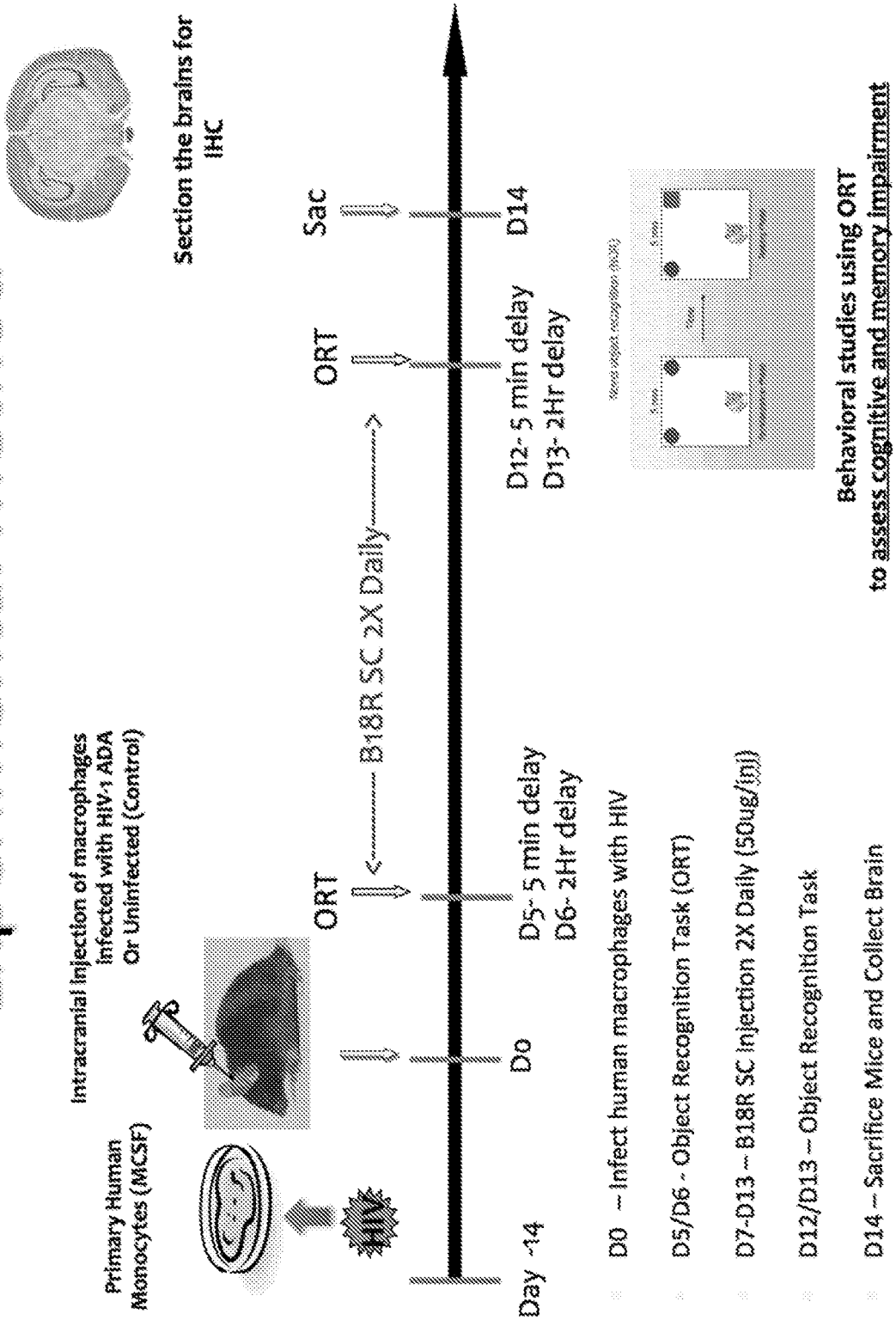
FIG. 2 is a schematic of methods in experiment 2.

Four-week old B6.CB17-Prkdcscid/SzJ male mice were injected IC (Day 0 or DO) in to the right frontal lobe with 105 HIV-infected or uninfected macrophages (FIG. 2). There were three groups of mice, control group (n=9), HAND mice without treatment (n=9), and HAND mice with B18R treatment (n=9). On D4 the mice experienced 10 minutes of acclimatization to a Plexiglas chamber (60 cm×60 cm). On D5 the procedure consisted of a training phase, followed by a preference test after a delay of 5 min (FIG. 3). In the training phase, duplicate copies of an object were placed near the two corners at opposite sides of the arena (15 cm from each adjacent wall). The animal was placed into the arena and allowed a total of 5 minutes of exploration of the two identical objects (FIG. 2A). During preference test or novel object testing (5 min duration), the animal was replaced in the arena, presented with two objects in the same positions: one object was one of the identical objects used in the training phase (A), and the other object was a novel object (B). Exploration times were recorded and used to calculate a discrimination index [time spent with object A minus time spent with object B]/[total time exploring both objects] for the training session and for the test session. Discrimination indices of 0 indicate equal exploration of both objects.

Figures 3A, 3B, 3C, 3D:
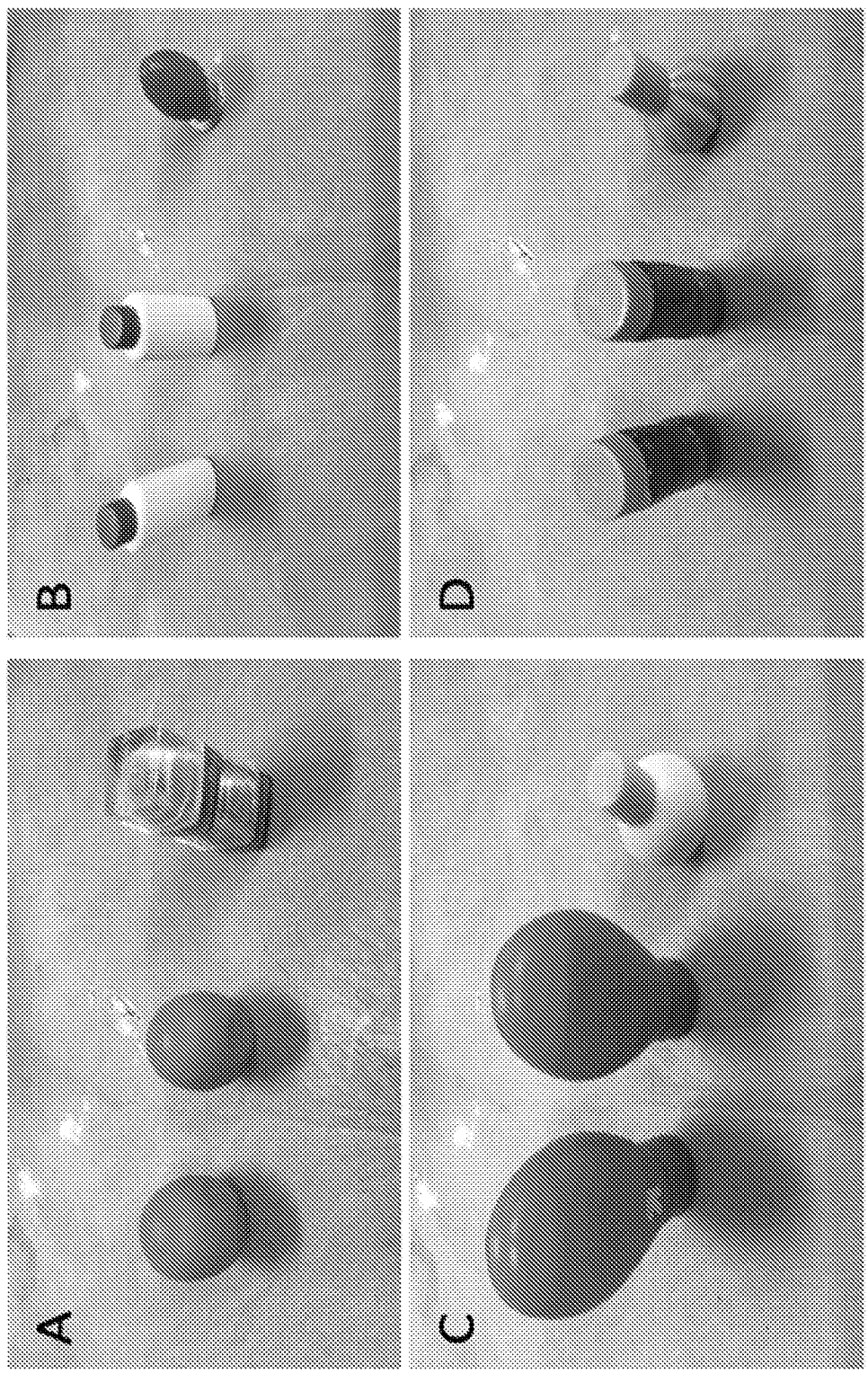
FIGS. 3A, 3B, 3C, and 3D show identical and novel objects in ORT. A. Day 5 B. Day 6 C. Day 12 D. Day 13

On the next day (D6) all mice were shown two different identical objects (different from identical object pair in training phase on D5)(FIG. 2B) in the training phase and after a 2 hr. delay the original object and a novel object for the testing phase. From D6-D13 mice HAND mice and control groups were given 200 ul saline SC BID. B18R treatment was given 200 ul of B18R (50 ug/inj) SC BID to another group of HAND mice. On D12 all mice were given a training phase followed by a 5 minute delayed preference test (FIG. 2C). On the next day (D13) mice were given a training phase and then after a 2 hour delay given a preference test. All objects used on all days were used only for that day (FIG. 3D). Treatment continued during training and testing D12 and D13. Mice were sacrificed on D14 after testing was completed and brains were snap frozen.

2. Results

Figures 4A, 4B, 4C, 4D:
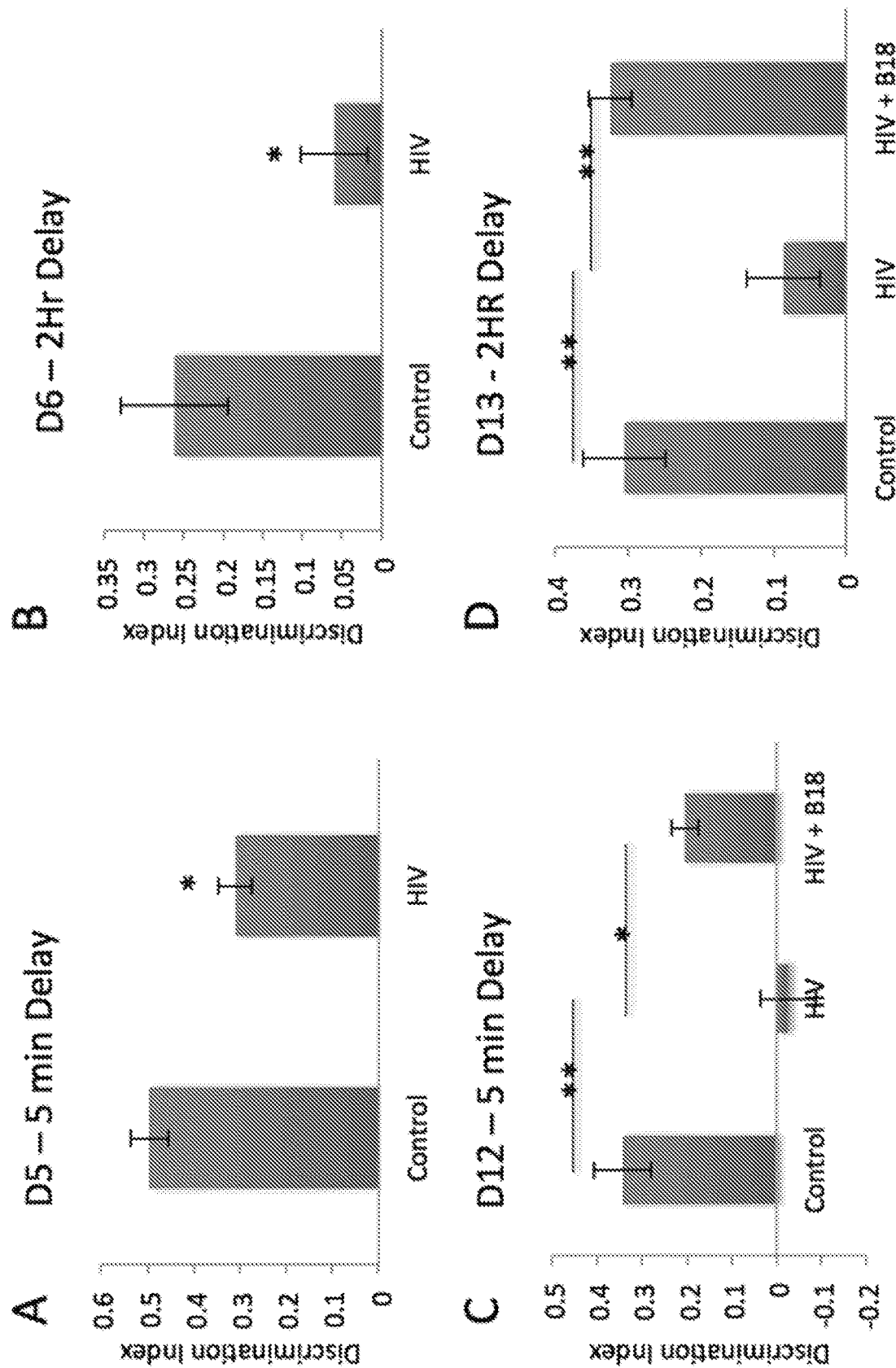
FIGS. 4A, 4B, 4C, and 4D are graphs showing the discrimination index for novel object testing (A), Day 5 (B), Day 6 (C) Day 12, (D) Day 13. $* \, p <0.05$, $**p<0.01$

On D5 all mice can discriminate novel vs familiar object (FIG. 4A). However, controls discriminate better than HAND mice. On D6 control mice discriminate substantially better than HAND mice on a more difficult ORT (2 hr delay) test (FIG. 4B). On D12, control and B18 treated HAND mice discriminate but untreated (receiving saline) HAND mice were not able to discriminate the 5 min ORT delay test (FIG. 4C). This is in contradistinction to D5 when untreated HAND mice were able to discriminate objects. On D13 after a 2 hr delay B18R treated HAND mice discriminate objects significantly better than untreated (saline) HAND mice (FIG. 4D).

3. Conclusions

B18R plus cART is superior to cART alone in ameliorating brain histopathology in this HAND mouse model. These abnormalities include potentially important markers in HAND such as astrogliosis, microgliosis and dendritic simplification. Astroglia and microglia represent cells types that are activated during HIV infection of the CNS and produce neurotoxins, including IFNα, that adversely affect neurons. Furthermore, the findings are important because if B18R is shown to be safe and effective in humans with HAND, it would be used as an add-on treatment.

The second experiment shows that B18R significantly reverses behavioral abnormalities in HAND mice. Novel agents tested in animal models of HAND ideally should show reversibility of behavioral abnormalities. There are several reasons that support this assertion. ANI and MND are the most common forms of HAND and by definition represent cognitive disorders that are relatively subtle compared to dementia. Like mild cognitive impairment in Alzheimer's disease, ANI and MND likely can lead to HAD and early treatment could prevent or slow progression. Because HAND mice do not have overt behavioral disturbances and need behavioral testing to demonstrate abnormalities, they are comparable to humans with ANI and MND. Early cognitive disturbances in HAND can be reversible with cART, representing neuronal dysfunctional, not death. The data presented in our second study are analogous to reversing cognitive dysfunction in humans with HAND.

Like previous clinical and translational studies that support the role of IFNα in HAND, the data presented here provide additional evidence that IFNα is produced and is neurotoxic during HIV infection of the brain. We believe our studies provide substantial impetus to precede to a Phase I trial of B18R in patients with HAND.

Example 2

Reversing Interferon-Alpha Neurotoxicity in a HIV-Associated Neurocognitive Disorders Mouse Model 1. Introduction HIV-associated neurocognitive disorders (HAND) remain a concern even in the combined antiretroviral therapy (cART) era. HAND affects approximately half of people living with HIV. In cART patients milder forms of HAND (e.g. mild neurocognitive disorder) are predominant. These milder forms of HAND eventually lead to HIV associated dementia, which results in substantial morbidity and mortality. Another concern is with prolonged life due to cART, aging HIV-infected individuals are more susceptible to cognitive decline. Associated comorbidities likely accelerate this process. Therefore, there is a need to develop adjunctive [to cART] therapies for HAND.

A model of HIV encephalitis (HIVE) was developed and refined to include behavioral parameters, which reflect cognitive deficits in humans with HAND. This model enabled testing of cART and its effects on histopathology and mouse behavior. Other studies in HAND mice correlated behavioral and histopathological findings with the presence of IFNα in mouse brain. These mouse studies were undertaken because clinical research has indicated that IFNα is present in the brains of patients with HIVE (i.e., pathological studies) and HAND, and that IFNα cerebrospinal fluid levels correlate with cognitive dysfunction. IFNα also correlates with behavioral abnormalities in HAND mice; these behavioral abnormalities and the corresponding histopathological features were prevented when neutralizing antibodies to IFNα or when a novel IFNα binding protein, B18R, were administered systemically.

In vitro studies have shed light on the mechanisms of IFNα neurotoxicity. Exposure of rat neuronal cultures to IFNα results in dendritic simplification, which is mediated through both the Type I IFN receptor (IFNAR) and the NMDA receptor (NMDAR). Furthermore, the GluN2A subunit of the NMDAR is specifically involved in IFNα neurotoxicity. Determining the mechanisms of IFNα neurotoxicity is important. Indeed, these mechanisms could be generalizable to other neurodegenerative diseases, and blocking IFNα directly may not be practical in humans, depending on the exact disease and individual patient responses.

Taking these considerations into account, it was determined if IFNα neurotoxicity is reversible in HAND mice. Here refinements of the HAND model are presented using object recognition tasks (ORT). ORT has enabled testing of B18R after behavioral abnormalities develop in HAND mice to determine reversibility of ORT abnormalities. This is a critical component of animal model testing since it reflects what would occur when treating patients who are discovered to have HAND. In addition, an in vitro rat neuronal system was used to further investigate the effects of IFNα on dendritic structure, specifically the presence of Post Synaptic Density (PSD)-95 in dendritic spines and the possible signaling mechanisms involved in IFNα neurotoxicity.

2. Methods i. In Vitro:

a. Rat Neuronal Cultures:

Rat neurons were either obtained from Brain Bits (Cat #SDECX; embryonic day 18) and cultured in NBACTIV1 media (Cat #nbactivl) until day 14, when they are relatively "mature", or cortical neurons were prepared from embryonic day 18 Sprague Dawley fetuses. Two different densities of neurons were utilized, based on test procedures. For PSD-95 puncta, low density cultures (10,000 neurons/cm') were placed on 12 mm poly D Lysine (Sigma cat #2636) coated coverslips, incubated in wells with glia (astrocytes) or removed for IFNα (300 IU/ml) exposure. High density cultures (500,000 neurons/60 mm dish) were used for protein extraction. These cultures contained approximately 2-3% glia (GFAP immunostaining).

b. SDS-PAGE/Western Blotting:

Protein samples (5 to 10 micrograms) were resolved in Criterion precast gels (Bio-Rad) and transferred to a PVDF membrane using a semidry system (Bio-Rad). All blocking antibody and washing steps were performed at room temperature (RT) on a rocker. Membranes were incubated for one hour in 3% non-fat dry milk in TBST (25 mM Tris, 140 mM NaCl, 3 mM KCl, and 0.05% Tween-20), then 4 hr in anti-Arf1 antibody (cat #ARP75924_P050, Aviva; 1:1000) diluted in 1% non-fat dry milk in TBST. Membranes were briefly washed in TBST followed by 3 separate 5 minute incubations in TBST. Membranes were incubated for one hour with goat anti-rabbit IgG HRP (cat #NEF812001EA, Perkin Elmer 1:5,000) diluted in 1% non-fat dry milk in TBST. Final washing included a quick rinse with ddH2O, 2 min wash in TBST, 4 min wash in TBST, and 5 min wash in 1× TBS. Immunoreactive bands were detected with chemiluminescence using ECL Prime substrate (cat #RPN2236, GE Healthcare Life Sciences) on a Chemidoc imager (Bio-Rad), and quantified with ImageJ (NIH). Arf1 signal was normalized to GAPDH Western blot (WB) intensity (cat #MAB374, Millipore;1:20,000).

c. PSD-95:

Rat neurons were seeded on poly-L-lysine coated coverslips and co-cultured with astroglia. On day 14, half of the conditioned medium from co-culture was transferred to new 6 well plates. To the conditioned medium, IFNα (300 IU/mL) or sterile water (used to reconstitute IFNα) was added, and coverslips with neurons were transferred from co-culture plates and placed in IFNα-(or vehicle-) containing plates. After 20 min or 2 hrs, neurons on coverslips were rinsed once in 1× PBS at RT and fixed in fresh 4% paraformaldehyde in 1× PBS for 5 minutes and rinsed in 1× TBS. Neurons were permeablized in 0.3% Triton X in 1× TBS, blocked with 2% goat and 2% horse serum in 1× TBS, and incubated with antibodies against MAP2 (cat #5622 Millipore and 1:100) and PSD-95 (cat #NB300-556 Novus Biologicals and 1:1000) in buffer (2% BSA in 1× TBS). Secondary antibodies were fluorescein-conjugated for MAP2 (cat #FI-1000, Vector Laboratories) and Texas Red-conjugated for PSD-95 (cat #TI-2000, Vector Laboratories) and applied for 30 minutes at 1:1000 in antibody buffer. After mounting in antifade reagent, images of 5 neurons/coverslip (i.e., 10 neurons/treatment group) were taken on an Olympus BX51 with Olympus DP80 camera. PSD-95 puncta were identified and counted with SYNPANAL software. For each neuronal image, dendrites were traced a distance of 40 linear units (SYNPANAL defined unit) starting at the first branch point of the dendrite from the soma. PSD-95 puncta along the region were counted and divided by the length to obtain PSD-95 puncta/unit. For each neuron PSD-95 puncta/unit was computed from the dendrites traced for that neuron (2 to 4). For each treatment, the average puncta/unit was determined by averaging the puncta/unit for each neuron (at least 10/treatment in each replicate plate). For each treatment within the experiment, the average puncta/unit is determined by averaging the puncta/unit for each replicate of that treatment (thus, n=3/treatment) for 20 min and 2 hours.

d. AMPA Receptor Immunofluorescent Staining:

Rat neurons were fixed with 4% paraformaldehyde in PBS for 20 min at RT. They were incubated with anti-GLuR2 (EMD Millipore, Burlington Mass.; 1:100), a subunit of the AMPA receptor (AMPAR), for 1 hour at RTO in the dark. After washes, this was followed by incubation with DAPI 500 mM 17 (Images were subjected ImageJ software for densitometric analysis).

e. Proteomics:

For proteomic analysis of total protein, rat cortical neurons were cultured in 60 mm dishes in high density (described above). After 14 days, cells were treated with 300 IU/mL IFNα for 20 min, 2 hr, 8 hr, 24 hr, or 48 hr. For comparison of the proteome, untreated cells were given sterile, distilled water (vehicle) equal to the volume of IFNα.

After incubations, cells were washed once in RT phosphate buffered saline (PBS) and scraped into 500 microliters of PBS. Cell slurries were snap frozen in a dry ice ethanol bath and processed by the Emory University Proteomics Core.

Figure 8:
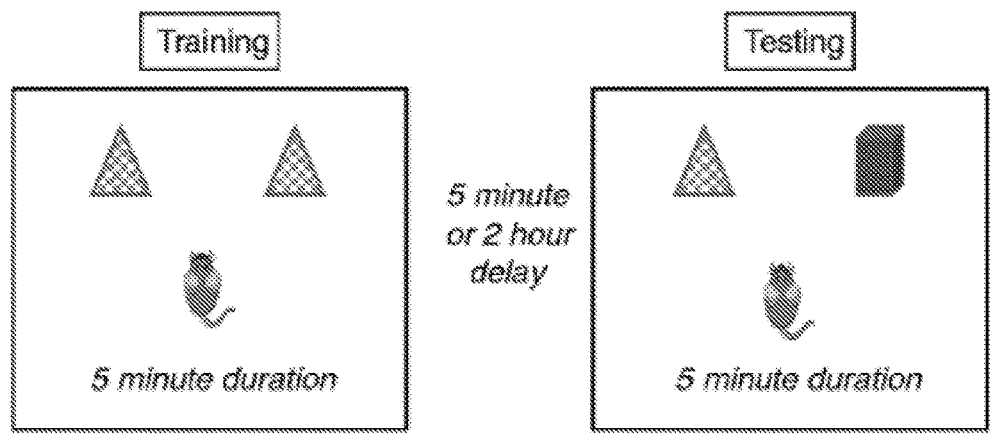
FIG. 8 shows a schematic depicting the methodology of the ORT with the treatments and tests for each day (day =D). For example, D5 represents day 5 after IC inoculation of human cells.
Figure 8:
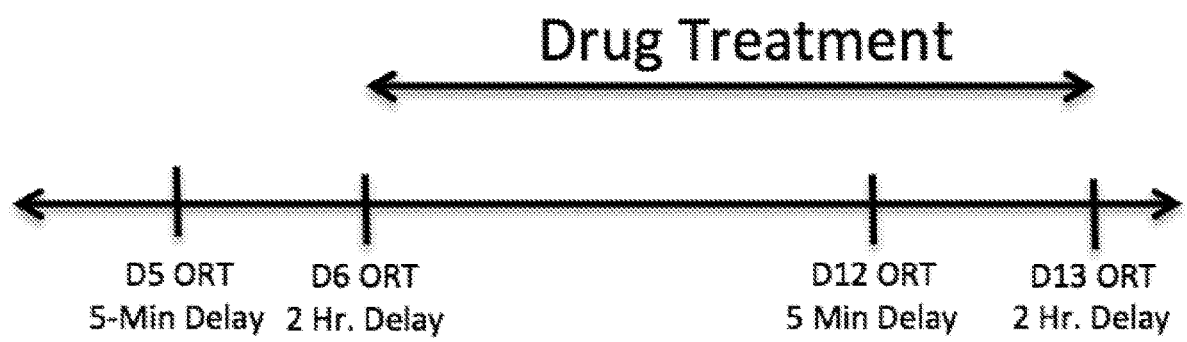

To select proteins for further analysis, GO-Elite software was used. GOElite identified gene ontology (GO) terms as significantly down-regulated by analyzing lists of protein accession numbers from each data set (20 min, 2 hr, 8 hr, 24 hr, 48 hr) and comparing to a list of accession numbers from the vehicle-treated sample. These lists of accession numbers were derived by identifying proteins for which the total peptide spectral match (PSM) was seven-fold (or more) lower in the IFNα treated sample than in the control sample. The Arf1 protein belonged to groups of GO terms (primarily G-protein signaling) that were down-regulated for all IFNα treated cultures and for which a relationship to neuron projections had been established. Thus, Arf1 was selected for WB analysis.

ii. In Vivo:

a. Animals:

Five week old B6.CB17-Prkdc/Szj (SCID) male mice were purchased from Jackson Laboratory (Bar Harbor, Me.), singly housed in sterile micro-isolator cages and given 1 week to acclimate before experimentation. All protocols were approved by the Atlanta VA Institutional Animal Care and Use Committee. SCID mice carry the severe combined immune deficiency mutation (caused by a spontaneous mutation in the Prkdc gene) on the C57BL/6J strain background. These mutant mice do not have functional T or B cells (lack the T cell receptor and competent antibody), thus supporting allogeneic and xenogeneic grafts.

b. Infection:

Purified, primary human monocytes ($1 \times 10^8$) were purchased from Dr. Howard Gendelman, University of Nebraska, and grown in Dulbecco's modified eagle medium. After 7 days, half (approximately $5 \times 10^7$) of the cells were infected with HIV-1ADA. The uninfected and infected human monocytes were cultured for 2 weeks. To determine the in vitro infection rate, infected cells on slides were stained for p24 antigen (see "Tissue Sectioning and Immunostaining" for methods). About 90% of the cells expressed p24. Infected and uninfected human monocyte derived macrophages (MDM) were resuspended in sterile PBS at 100,000 cells per 30 pl for inoculation. Infected (HIV or HAND mice) and uninfected MDM (Control mice) were injected intracerebrally (IC) into the right frontal lobe.

c. Antiretroviral Drug Preparation and B18R Drug Preparation:

Atazanavir (Bristol-Meyers Squibb) was dissolved in sterile water at a concentration of 5 mg/ml. Tenofovir (Gilead Sciences, Inc.) was dissolved in sterile water at 13 mg/ml. Emtricitabine (Gilead Sciences, Inc.) was dissolved in sterile water at 100 mg/ml. As atazanavir would not dissolve with tenofovir and emtricitabine, it was injected into mice subcutaneously (SC) separately. Dosages for the antiretroviral drugs (ARV) were based on a previous study showing them to be effective and measurable in the brain after systemic administration. B18R (Normferon™, a gift from Meiogen Biotechnology Corp.) was produced using modified standard recombinant procedures and purified to a single band on a PAGE gel using cation exchange. For in vivo potency estimation, a test of B 18R was run in non-immunocompromised animals. Each mouse of the HIV-B18R group received 50 μg of B18R per day suspended in 300 uL of PBS in divided doses (150 μL×2 times a day), which was given either from the time of human MDM IC inoculation (cART plus B18R histopathological study—see below) or 6 days later (Behavioral study—see below) until the mice were sacrificed. B18R concentration was measured using the microBCA assay (Thermofisher). Serum half-life was estimated using IFN ELISA measurements (PBL kit) in polyI:C (EMD Millipore) induced C57/BL6 mice. The time point after B18R injection at which the B18R could no longer reduce serum IFN by 50% was used as a preliminary guide to serum half-life (4.5 hours). B18R crosses the blood brain barrier and is detectable in brain parenchyma.

d. Antiretroviral & B18R Therapy:

For the histopathological study, there were four groups of mice: control group (n=9), HIV infected without treatment (n=9), HIV infected with antiretroviral (ARV=cART) treatment (n=7) and HIV infected with both ARV and B18R treatment (n=7). All mice received SC injections for 10 days of either 0.9% NaCl (n=12) or ARV at a dose of 75 mg/kg/injection (inj) (n=12). This dose was based on a previously published experiment 20. ARV injections started immediately following IC inoculation of HIV-infected or uninfected human MDM. ARV was administered at 7:30 AM, 11:30 AM and 3:30 PM. Immediately after IC inoculation with either infected or uninfected MDM, HIV infected mice in the ARV and B18R group also received B18R treatment. Each mouse received 2 SC injections of B18R per day over a period of 10 days at 9:30 am and 1:30 AM. Mice were sacrificed on D10 following the final injections. Brains were snap frozen for tissue sectioning.

e. Behavioral and B18R Treatment Study:

Four-week old B6.129S7-Rag 1 tml Mom/J male mice were injected IC (Day 0 or DO) with $10^5$ HIV-infected or uninfected human MDM (Supplemental FIG. 1). There were three groups of mice: control group (n=9), HIV infected without treatment (n=9), and HIV infected with B18R treatment (n=9). From D6 through D13, mice in HIV and control groups were given 200 ul saline SC BID. Mice in the B18R treatment group were given 200 ul of B18R (50 ug/inj) SC BID.

f. Object Recognition Behavioral Testing:

On D4 the mice experienced 10 minutes of acclimation to the Plexiglas chamber (60 cm×60 cm) used for all object recognition training and testing. On D5 the procedure consisted of a training phase, followed by a 5 minute delay, and then a preference test (FIG. 8). In the training phase, duplicate copies of an object were placed near the two corners at either end of opposite sides of the arena (15 cm from each adjacent wall). The animal was placed into the arena and allowed 5 minutes of exploration of objects. During preference/novel object testing (5 minute duration), the animal was replaced in the arena, presented with two objects in the same positions: one object was one of the identical objects used in the training phase (A), and the other object was a novel object (B). For data scoring, the analyst was blinded to treatment. Exploration times were recorded and used to calculate a discrimination index [time spent with object A—time spent with object B]/[total time exploring both objects] for training and test sessions. Discrimination indices of 0 indicated equal exploration of both objects. On the next day (D6) all mice were shown two different identical objects in the training phase, and after a 2 hour delay, an old and novel object in the testing phase. From D6 through D13, mice received treatments. On D12, all mice were given a training phase, a 5 minute delay, and then a preference test. On the next day (D13) mice were given a training phase, a 2 hour delay, and then a preference test. For any given day, all utilized objects were used only for that day. Treatment continued during training and testing for D12 and D13. Mice were sacrificed on D13 after testing was completed.

g. Tissue Sectioning and Immunostaining:

Mouse brains (B18R plus ARV study only) were sectioned and stained. Briefly, starting rostrally (frontal lobe), fifty 5 μm coronal sections were stained using an immunoperoxidase method for HIV (p24, 1:20, Dako), human macrophages (EBM11, 1:50, Dako), astrogliosis (anti-glial fibrillary acidic protein or GFAP, 1:750, Millipore), mouse mononuclear phagocytes (CD45, 1:50, AbDSerotec), and neurons and processes (anti-microtubule-associated protein 2 or MAP 2, 1:200, Millipore). The sections were examined under light microscopy (Olympus BX51).

h. Densitometry:

The evaluator was initially blinded to treatment status. Microscopic images of the tissue sections were taken at varying magnifications: GFAP at 4x and MAP 2 and CD45 at 20X. Each image consisting of 900 X 672 pixels was captured using Image-Pro Express software on a Windows computer. Tiff images were imported into NIH ImageJ. They were then set to 8 bit mono, the correct measurement parameters set, and the desired area of tissue was selected and measured. The intensities of the treatment group sections were compared to the control and HIV+ untreated sections. MAP2 expression was examined differently. MAP2 sections with reduced staining in the area of the xenograft within the right hemisphere were compared via densitometry with similar anatomical areas of the uninoculated left hemisphere to determine the percent decrease in MAP-2 expression.

i. Statistical Analyses:

SPSS software was used for statistical analyses. An analysis of variance (ANOVA) with Tukey's post hoc test was used to compare differences in pathology. A t-test was used to compare differences in viral load of p24 counts. A two-way repeated measures ANOVA model was used to analyze PSD95 puncta density using GraphPad Prism 7. Factors were treatment (interferon and vehicle) and time (20 min and 2 hr). Data were paired within each of the 3 separate neuron preparation batches. A post-hoc test p value of <0.05 was considered significant for in vitro and in vivo experiments. An analysis of variance (ANOVA) with Tukey's post hoc test was used to compare differences in behavior. A p value of <0.05 was considered significant.

Figure 5:
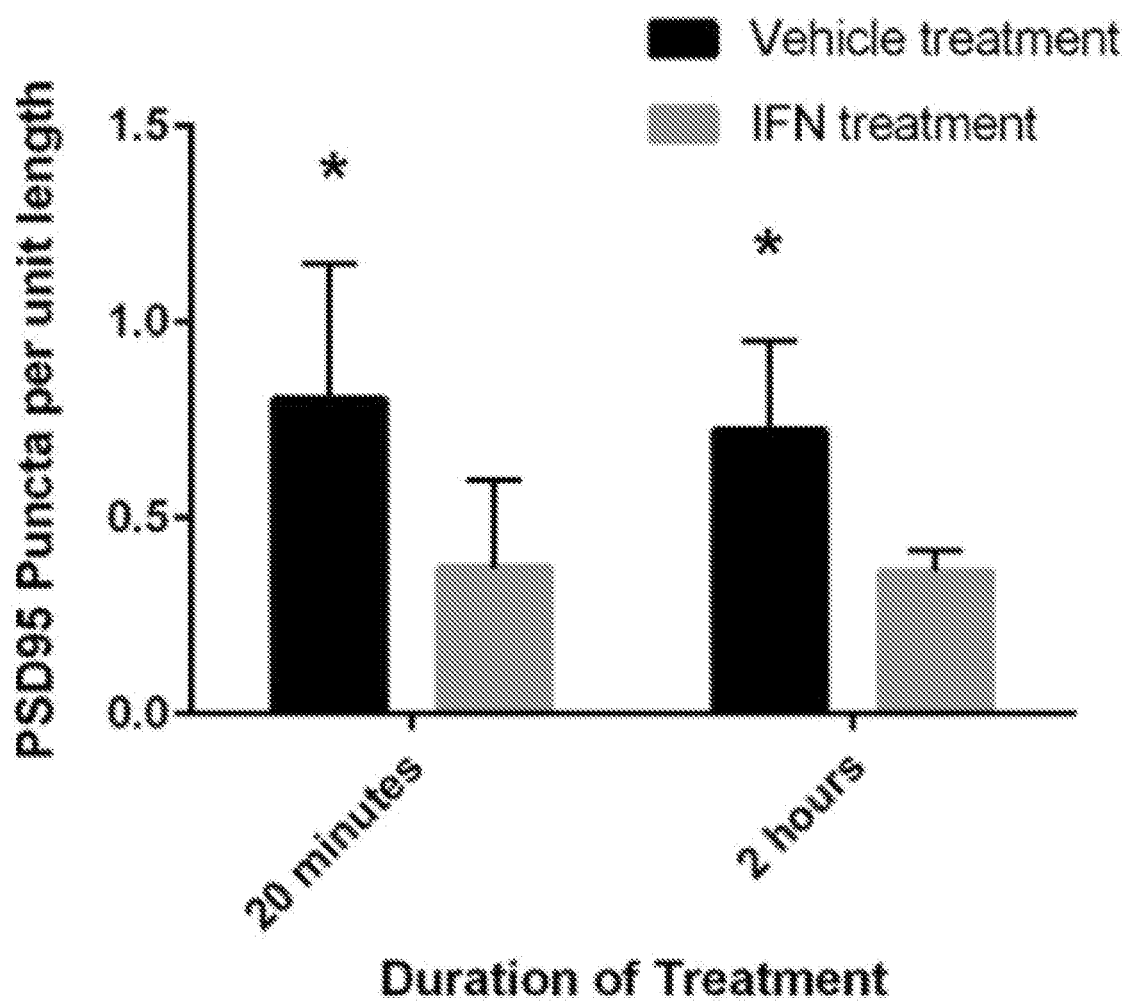
FIG. 5 is a graph of PSD95 puncta per unit length vs duration of treatment. PSD-95 puncta in vehicle treated and IFNα treated neuronal cultures averaged over 3 separate experiments. PSD-95 puncta were counted by a blinded observer and these numbers were averaged for each experiment. $*p<0.05$.
Figure 6:
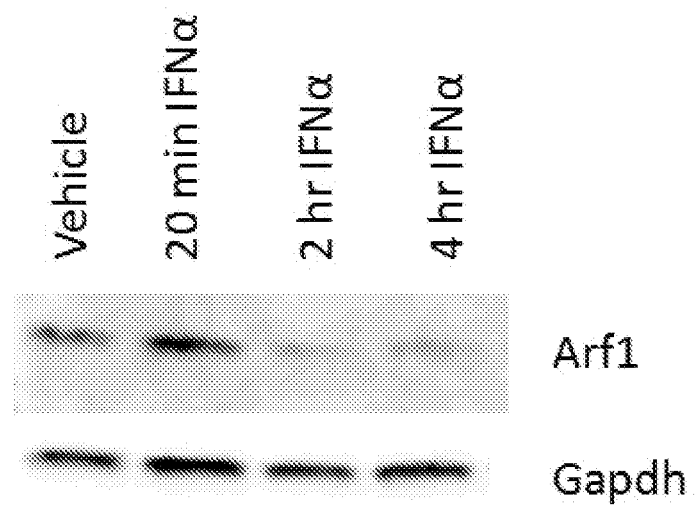
FIG. 6 is a representative Western Blot of Arfl expression from vehicle treated and IFNα treated (300 IU/ml) rat neurons for various times. Representative of 3 experiments. Gapdh=glyceraldehyde 3-phosphate dehydrogenase.
Figures 9A, 9B, 9C, 9D, 9E, 9F, 9G, 9H:
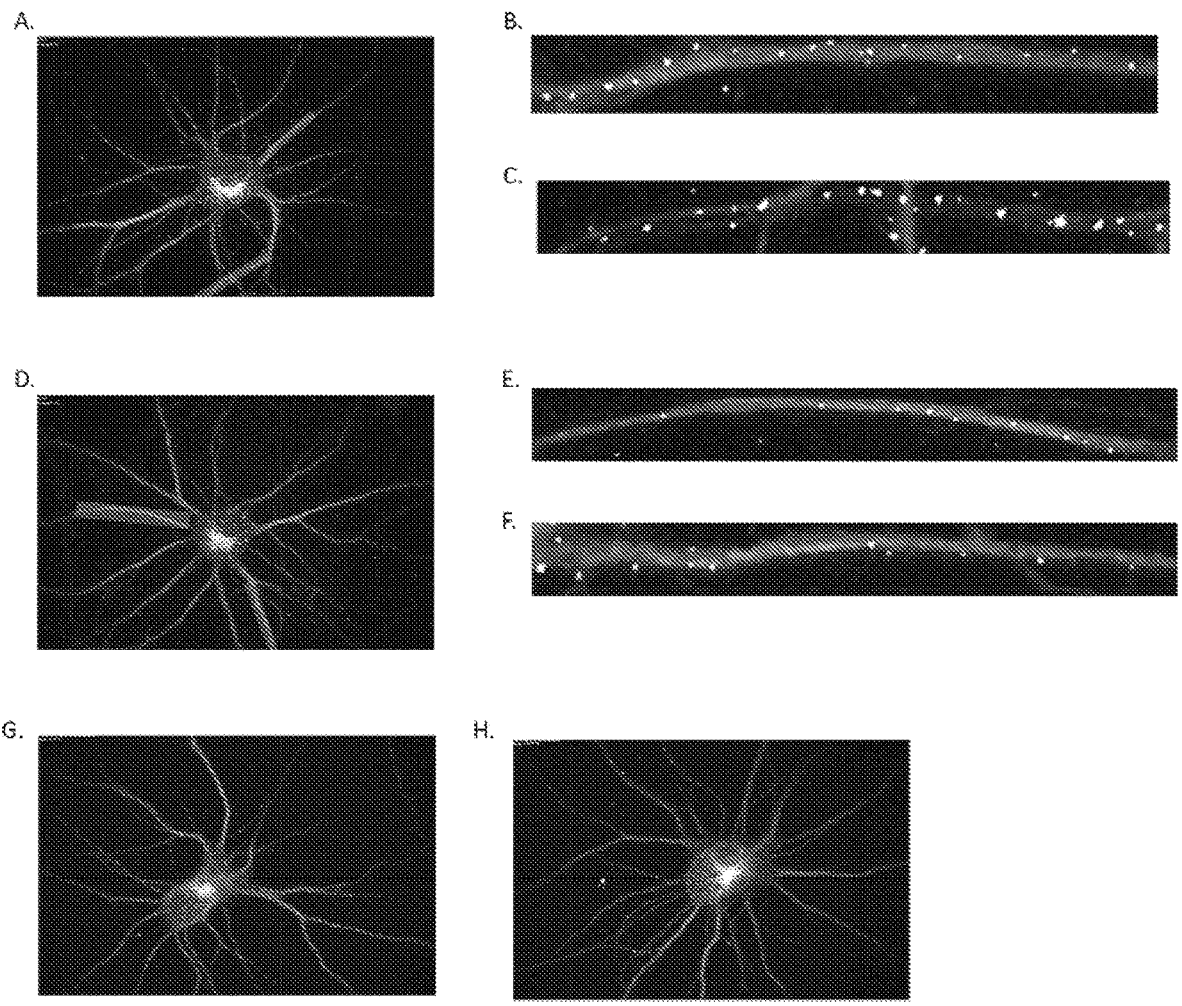
FIGS. 9A-9H show representative images of rat neurons double-stained for PSD-95 and MAP2. (A) sham control neuron (20× magnification). (B&C) selected dendrites from control neuron (A) (100× magnification), (D) representative neuron after 2 hours of treatment with IFNα (20× magnification), (E&F) selected dendrites from IFNα treated neuron (D). (G) representative neuron from 20 minutes sham control group, and (H) a representative neuron, 20 minutes after treatment with IFNα. Threshold was adjusted to accept PSD-95 puncta brighter than 140 (255 maximum brightness). Pixels above threshold are colored white and counted as PSD-95 positive puncta.

3. Results i. B18R Reverses Behavioral Abnormalities in HAND Mice:

On Day 5, all mice could discriminate the novel vs. familiar object. However, Control mice (injected IC with uninfected human MDM) discriminated better than HAND mice (injected IC with HIV-infected human MDM; data not shown). On Day 6, only Control mice discriminated on the more difficult ORT 2 hour delay test (FIG. 4B); HIV (i.e., HAND) mice could not discriminate the novel object with this increased temporal demand. On D12, Control and B18R treated mice discriminated, but untreated (saline) HIV mice did not discriminate the ORT test with the 5 min delay, which they were once able to discriminate on Day 5 (data not shown). On D13, HIV mice that were once unable to discriminate on D6 (FIG. 4B), now having been treated with B18R for 6 days, discriminated on D13 during a more difficult ORT task (FIG. 4D). Untreated HIV mice were unable to discriminate on 2 hr delay ORT on Day 6 and Day 13.

ii. B18R Plus cART Improves HAND Histopathology:

B18R plus ARV significantly prevents astrogliosis compared to HAND (labeled "HIV" in FIG. 1) mice (injected with HIV-infected human MDM) given saline (FIG. 1A). Immunostaining for the presence of mouse mononuclear phagocytes is also significantly attenuated by B18R plus ARV treatment compared to HAND mice given saline (FIG. 1B). Finally, a marker of neuronal dendrites (MAP2) is relatively preserved in HAND mice given B18R plus ARV compared to saline (FIG. 1C). In contrast, HAND mice treated with ARV (FIG. 1 A, B and C, HIV+ARV columns) were not statistically different from HAND mice given saline (HIV-saline), although results suggest improvement of histopathology in HAND mice given ARV relative to saline only.

iii. IFNα Decreases PSD-95 puncta on Rat Neurons:

Twenty minutes and 2 hours after IFNα exposure PSD-95 puncta are significantly decreased on rat neurons compared to control neurons (FIG. 5 and FIG. 9).

iv. IFNα Decreases Arf1 in Rat Neurons:

Proteomic analyses revealed decreased Arf1 levels in rat neuronal cultures exposed to IFNα. FIG. 6 depicts WB verification of proteomics data and is representative of 4 experiments. There are decreases in Arf1 at 2 and 4 hours after IFNα exposure. Arf1 was also decreased at 8 hours, but not consistently at 24 hours (data not shown).

v. IFNα Decreases AMPA Receptor Expression on Rat Neurons:

Rat neuronal surface expression of AMPARs is significantly decreased in rat neurons exposed to IFNα for 2 hours (FIG. 7). Data are representative of 2 separate experiments 4. Discussion B18R is a biologic cloned from the Vaccinia virus and is able to bind Type I IFNs with high affinity (Kd 174 pM) 21. When B18R was administered to HAND mice after they developed behavioral deficits on the ORT (FIG. 4), it reversed these behavioral abnormalities after 6 to 7 days of treatment. When B18R was combined with a cART regimen, important histopathological features of HAND mice, such as increases in microgliosis and astrogliosis, and decreases in the neuronal marker MAP2, were ameliorated (FIG. 1). These data also indicate that B18R, when combined with cART, improves pathological markers of HAND to a greater extent than cART alone.

These findings are consistent with previous studies showing that systemic treatment with either neutralizing antibodies to IFNα or B18R essentially prevents behavioral and histopathological abnormalities in HAND mice respectively. More importantly, they extend previous findings by showing that B18R can reverse behavioral deficits, and when combined with cART, likely improves HAND pathology more than cART alone. It was not tested whether cART alone could improve behavior because it was previously demonstrated that it had no effect in the HAND model. The significance of this preclinical testing of B18R is that in a practical clinical setting, HIV infected patients are often already taking cART and must first be identified with HAND before a specific cognitively targeted treatment can be initiated. The data indicate that in cART HIV patients, B18R treatment could be introduced after cognitive dysfunction is detected. Moreover, the current data, combined with the landscape from prior research, indicate that this combination treatment would result in improvement of symptoms such as concentration and memory impairment and demonstrate a strong impetus for Phase I testing in HAND patients.

Although there is evidence that people living with HIV with increased systemic IFNα levels may have worse clinical outcomes, there is concern that inhibiting Type I IFNs (e.g., B18R treatment) could result in increased viral loads, even in patients already receiving cART. There could be other untoward effects of inhibiting Type I IFNs, such as increased susceptibility to other infections. With this in mind, the mechanisms of IFNα neurotoxicity was investigated with the idea that this can lead to the development of novel therapeutics that are more specific in preventing neuronal dendritic simplification and better tolerated. In addition, these treatments might be more applicable to a broad spectrum of neurodegenerative diseases.

It is believed that alterations in neuronal dendrites and synapses in vitro are reflections of neuronal connectivity in vivo, and that the ability of neurons to make connections through healthy dendrites and synapses is representative of cognitive functions. Previous in vitro studies demonstrated that exposure of rat neurons to IFNα results in shortened dendritic processes with less branching. The current findings of decreased PSD-95 on dendritic spines (FIG. 5) expands previous findings to a fundamental element of neuronal transmission and memory: the synapse. PSD-95 is present on dendritic spines and increases in spine density likely reflect memory consolidation. Conversely, decreased dendritic spine density has been found at autopsy in patients with HIV encephalitis.

Arf1 is also decreased in neurons exposed to IFNα (FIG. 6). Arf1 is a small GTP binding protein and blocks PICK1, which inhibits Arp2/3. Arp2/3 promotes F-actin stabilization of PSD-95 complexes and AMPA receptors. In addition, it was found that after 2 hours of IFNa exposure rat neurons exhibited reduced expression of AMPARs (FIG. 7). By decreasing Arf1, IFNα can destabilize F-actin resulting in decreases in PSD-95 expression, leading to AMPA receptor internalization. This results in decreased plasticity and long-term depression in affected neurons, and thus, cognitive dysfunction. However, the time sequence of decreased Arf1 (starting 2 hrs after IFNα exposure) and decreased PSD-95 puncta (starting at 20 min after IFNa exposure) shown in this study indicates that either Arf1 decreases are unrelated to reduced PSD-95 expression, or that there are two mechanisms leading to decreased PSD-95 expression and decreased surface AMPAR expression that are occurring in parallel. In either case, the in vitro findings indicate that signaling pathways leading to decreases in PSD-95 expression and loss of surface AMPAR expression are fundamental to cognitive dysfunction caused by IFNα.

In summary, the present findings and clinical data showing correlation of CSF IFNα levels with cognitive dysfunction in HAND patients lend substantial support for a Phase I trial of B18R in this patient population. In addition, there is growing evidence that IFNα plays a broader role in other neuroinflammatory and neurodegenerative disorders, such as Alzheimer's disease.

Those skilled in the art will recognize, or be able to ascertain using no more than routine experimentation, many equivalents to the specific embodiments of the method and compositions described herein. Such equivalents are intended to be encompassed by the following claims.

REFERENCES

1. Heaton R K, Clifford D B, Franklin D R, Jr., et al. HIV-associated neurocognitive disorders persist in the era of potent antiretroviral therapy: CHARTER Study. Neurology. 2010 Dec. 7; 75(23):2087-96.
2. Antinori A, Arendt G, Becker J T, et al. Updated research nosology for HIV-associated neurocognitive disorders. Neurology. 2007 Oct. 30; 69(18):1789-99.
3. Saylor D, Dickens A M, Sacktor N, et al. HIV-associated neurocognitive disorder-pathogenesis and prospects for treatment. Nat Rev Neurol. 2016 April; 12(4):234-48.
4. Grant I, Franklin D R, Jr., Deutsch R, et al. Asymptomatic HIV-associated neurocognitive impairment increases risk for symptomatic decline. Neurology. 2014 Jun. 10; 82(23):2055-62.
5. Rumbaugh J A, Tyor W. HIV-associated neurocognitive disorders: Five new things. Neurol Clin Pract. 2015 June; 5(3):224-31.
6. Tyor W R, Power C, Gendelman H E, Markham R B. A model of human immunodeficiency virus encephalitis in scid mice. Proc Natl Acad Sci USA. 1993 Sep. 15; 90(18):8658-62.
7. Avgeropoulos N, Kelley B, Middaugh L, et al. SCID mice with HIV encephalitis develop behavioral abnormalities. J Acquir Immune Defic Syndr Hum Retrovirol. 1998 May 1; 18(1):13-20.
8. Cook J E, Dasgupta S, Middaugh L D, et al. Highly active antiretroviral therapy and human immunodeficiency virus encephalitis. Ann Neurol. 2005 June; 57(6):795-803.
9. Cook-Easterwood J, Middaugh L D, Griffin W C, 3 rd, Khan I, Tyor W R. Highly active antiretroviral therapy of cognitive dysfunction and neuronal abnormalities in SCID mice with HIV encephalitis. Exp Neurol. 2007 June; 205(2):506-12.
10. Sas A R, Bimonte-Nelson H A, Tyor W R. Cognitive dysfunction in HIV encephalitic SCID mice correlates with levels of Interferon-alpha in the brain. AIDS. 2007 Oct. 18; 21(16):2151-9.
11. Fritz-French C, Tyor W. Interferon-alpha (IFNalpha) neurotoxicity. Cytokine Growth Factor Rev. 2012 February-April; 23(1-2):7-14.
12. Anderson A M, Lennox J L, Mulligan M M, et al. Cerebrospinal fluid interferon alpha levels correlate with neurocognitive impairment in ambulatory HIV-Infected individuals. J Neurovirol. 2017 February; 23(1):106-12.
13. Sas A R, Bimonte-Nelson H, Smothers C T, Woodward J, Tyor W R. Interferon-alpha causes neuronal dysfunction in encephalitis. J Neurosci. 2009 Mar. 25; 29(12): 3948-55.
14. Fritz-French C, Shawahna R, Ward J E, Maroun L E, Tyor W R. The recombinant vaccinia virus gene product, B18R, neutralizes interferon alpha and alleviates histopathological complications in an HIV encephalitis mouse model. J Interferon Cytokine Res. 2014 July; 34(7):510-7.
15. Kessing C F, Tyor W R. Interferon-alpha induces neurotoxicity through activation of the type I receptor and the GluN2A subunit of the NMDA receptor. J Interferon Cytokine Res. 2015 April; 35(4):317-24.
16. Tyor W R, Bimonte-Nelson H. A mouse model of HIV-associated neurocognitive disorders: a brain-behavior approach to discover disease mechanisms and novel treatments. J Neurovirol. 2017 Sep. 11.
17. Rui Y, Myers K R, Yu K, et al. Activity-dependent regulation of dendritic growth and maintenance by glycogen synthase kinase 3beta. Nat Commun. 2013; 4:2628.
18. Zambon A C, Gaj S, Ho I, et al. GO-Elite: a flexible solution for pathway and ontology over-representation. Bioinformatics. 2012 Aug. 15; 28(16):2209-10.
19. Rocca D L, Amici M, Antoniou A, et al. The small GTPase Arf1 modulates Arp2/3-mediated actin polymerization via PICK1 to regulate synaptic plasticity. Neuron. 2013 Jul. 24; 79(2):293-307.
20. Koneru R, Olive M F, Tyor W R. Combined antiretroviral therapy reduces brain viral load and pathological features of HIV encephalitis in a mouse model. J Neurovirol. 2014 February; 20(1):9-17.
21. Symons J A, Alcami A, Smith G L. Vaccinia virus encodes a soluble type I interferon receptor of novel structure and broad species specificity. Cell. 1995 May 19; 81(4):551-60.
22. Gringeri A, Musicco M, Hermans P, et al. Active anti-interferon-alpha immunization: a European-Israeli, randomized, double-blind, placebo-controlled clinical trial in 242 HIV-1-infected patients (the EURIS study). J Acquir Immune Defic Syndr Hum Retrovirol. 1999 Apr. 1; 20(4):358-70.
23. Utay N S, Douek D C. Interferons and HIV Infection: The Good, the Bad, and the Ugly. Pathog Immun. 2016 Spring; 1(1):107-16.
24. Benitez-King G, Ramirez-Rodriguez G, Ortiz L, Meza I. The neuronal cytoskeleton as a potential therapeutical target in neurodegenerative diseases and schizophrenia. Curr Drug Targets CNS Neurol Disord. 2004 December; 3(6):515-33.
25. Lin Y C, Koleske A J. Mechanisms of synapse and dendrite maintenance and their disruption in psychiatric and neurodegenerative disorders. Annu Rev Neurosci. 2010; 33:349-78.
26. Tada T, Sheng M. Molecular mechanisms of dendritic spine morphogenesis. Curr Opin Neurobiol. 2006 February; 16(1):95-101.
27. Masliah E, Ge N, Morey M, DeTeresa R, Terry R D, Wiley C A. Cortical dendritic pathology in human immunodeficiency virus encephalitis. Lab Invest. 1992 March; 66(3):285-91.
28. Masliah E, Heaton R K, Marcotte T D, et al. Dendritic injury is a pathological substrate for human immunodeficiency virus-related cognitive disorders. HNRC Group. The HIV Neurobehavioral Research Center. Ann Neurol. 1997 December; 42(6):963-72.
29. Taylor J M, Minter M R, Newman A G, Zhang M, Adlard P A, Crack P J. Type-1 interferon signaling mediates neuro-inflammatory events in models of Alzheimer's disease. Neurobiol Aging. 2014 May; 35(5):1012-23.

We claim:

1. A method of treating a subject with HW associated neurodegenerative disorder (HAND) comprising administering to the subject with HAND a therapeutically effective amount of B18R (SEQ ID NO:1) and combined anti-retroviral therapy (cART).

2. The method of claim 1, wherein administering a therapeutically effective amount of B 18R and cART occurs simultaneously.

3. The method of claim 1, wherein the subject with HAND has previously undergone cART treatment without administering B18R.

4. The method of claim 1, wherein the cART comprises atazanavir, tenofovir, and emtricitabine.

5. The method of claim 1, wherein the B18R and cART are administered subcutaneously.

* * * * *